(12) United States Patent
Nakamura et al.

(10) Patent No.: US 9,206,104 B2
(45) Date of Patent: Dec. 8, 2015

(54) METHODS FOR PRODUCING BICYCLIC COMPOUNDS VIA IMINIUM SALT

(71) Applicant: Daiichi Sankyo Company, Limited, Tokyo (JP)

(72) Inventors: Yoshitaka Nakamura, Kanagawa (JP); Kenichi Kimura, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 55 days.

(21) Appl. No.: 14/100,647

(22) Filed: Dec. 9, 2013

(65) Prior Publication Data

US 2014/0094624 A1 Apr. 3, 2014

Related U.S. Application Data

(63) Continuation of application No. PCT/JP2012/064415, filed on Jun. 5, 2012.

(30) Foreign Application Priority Data

Jun. 8, 2011 (JP) ................................. 2011-127957

(51) Int. Cl.
| | | |
|---|---|---|
| *C07C 45/41* | (2006.01) | |
| *C07C 227/34* | (2006.01) | |
| *C07C 229/32* | (2006.01) | |
| *C07C 45/52* | (2006.01) | |
| *C07C 51/38* | (2006.01) | |
| *C07C 211/63* | (2006.01) | |
| *C07C 227/22* | (2006.01) | |

(52) U.S. Cl.
CPC ................. *C07C 45/41* (2013.01); *C07C 45/52* (2013.01); *C07C 51/38* (2013.01); *C07C 211/63* (2013.01); *C07C 227/22* (2013.01); *C07C 227/34* (2013.01); *C07C 229/32* (2013.01); *C07C 2102/20* (2013.01)

(58) Field of Classification Search
CPC ...... C07C 45/52; C07C 51/38; C07C 49/627; C07C 57/03; C07C 2102/20; C07C 211/63; C07C 227/22; C07C 227/34; C07C 229/32; C07C 45/41
USPC ............................ 562/501; 564/291; 568/356
See application file for complete search history.

(56) References Cited

U.S. PATENT DOCUMENTS

| | | |
|---|---|---|
| 5,191,125 A | 3/1993 | Rosini et al. |
| 2003/0078300 A1 | 4/2003 | Blakemore et al. |
| 2003/0220397 A1 | 11/2003 | Bryans et al. |
| 2004/0152779 A1 | 8/2004 | Bryans et al. |
| 2006/0154929 A1 | 7/2006 | Anker et al. |
| 2010/0110361 A1 | 5/2010 | Matsuda et al. |
| 2010/0249229 A1 | 9/2010 | Shimada et al. |

FOREIGN PATENT DOCUMENTS

| | | |
|---|---|---|
| EP | 0 521 571 B1 | 9/1995 |
| JP | 2010-241796 A | 10/2010 |
| WO | 2009/041453 A1 | 4/2009 |
| WO | 2010/084798 A1 | 7/2010 |

OTHER PUBLICATIONS

Brannock ("The Chemistry of Isobutenylamines. II. Alkylation with Allylic and Benzyl Halides" J. Org. Chem., 26, 1961, p. 3576-3577).*
Carey B ("Advanced Organic Chemistry Part B: Reactions and Synthesis" Chapter 2, Reactions of Nucleophilic Carbon Species with Carbonyl Groups, 1977, p. 33-71).*
Carey A ("Advanced Organic Chemistry Part A: Structures and Mechanisms" Chapter 2, Stereochemistry, Conformation, and Stereoselectivity, 2007, 5th edition, p. 119-251).*
Hodgson et al., "Synthesis and C-Alkylation of Hindered Aldehyde Enamines," *J. Org. Chem.*, (2009), 74(3):1019-1028.
Hodgson et al., "Enamines from Terminal Epoxides and Hindered Lithium Amides," *J. Am. Chem. Soc.*, (2004), 126(22):6870-6871.
Snider et al., "Type III Intramolecular [2+2] Cycloadditions of Vinylketenes," *J. Org. Chem.*, (1988), 53(22):5320-5328.
Whittaker et a., "Asymmetric synthesis towards (3Z,6R)-3-methyl-6-isopropenyl-3,9-decadien-1-yl acetate, a component of the California red scale pheromone," *Can. J. Chem.*, (1985), 63(11):2844-2852.
Supplementary European Search Report issued Feb. 9, 2015 in European Application No. EP 12 79 6329, 7 pages.
Bryans et al., "Identification of Novel Ligands for the Gabapentin Binding Site on the $a_2\sigma$ Subunit of a Calcium Channel and Their Evaluation as Anticonvulsant Agents," *J. Med. Chem.*, 41:1838-1845 (1998).
Cook et al., "Preparation and 3-Aza-Cope Rearrangement of N-Alkyl-N-allyl Enamines," *J. Org. Chem.*, 56:5578-5583 (1991).
Elkik et al., "No. 164.—Mécanisme d'alcoylation des énamines," *Bulletin de la Société chimique de France*, 3:903-910 (1969).
Gee et al., "The Novel Anticonvulsant Drug, Gabapentin (Neurontin), Binds to the $a_2\sigma$ Subunit of a Calcium Channel," *J. Biol. Chem.*, 271:5768-5776 (1996).
International Search Report issued in PCT Application No. PCT/JP2012/064415 on Aug. 21, 2012, 2 pages.

\* cited by examiner

*Primary Examiner* — Jafar Parsa
*Assistant Examiner* — Amy C Bonaparte
(74) *Attorney, Agent, or Firm* — Dorsey and Whitney LLP

(57) ABSTRACT

The problem to be solved is to provide a method for producing a compound having excellent activity as an $\alpha_2\delta$ ligand. The solution thereto is a method for producing a compound represented by the general formula (VI) or a salt thereof via an iminium salt: [in the formula, $R^1$: a hydrogen atom or a C1-C6 alkyl group].

Formula 1

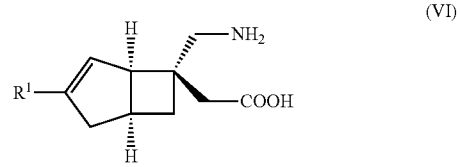

(VI)

8 Claims, No Drawings

METHODS FOR PRODUCING BICYCLIC COMPOUNDS VIA IMINIUM SALT

This application claims the benefit under 35 U.S.C. §111 (a) as a continuation application of International Application No. PCT/JP2012/064415, filed Jun. 5, 2012, entitled "Method for Producing Bicylic Compound via Iminium Salt," which claims priority to Japanese Patent Application No 2011-127957, filed Jun. 8, 2011, the contents of all of which are hereby incorporated in their entirety by reference.

TECHNICAL FIELD

The present invention relates to a method for producing a bicyclic γ-amino acid derivative or a pharmacologically acceptable salt thereof, particularly, a compound having activity as an $\alpha_2\delta$ ligand and an intermediate thereof.

BACKGROUND ART

Compounds that exhibit high-affinity binding to voltage-dependent calcium channel subunit $\alpha_2\delta$ have been shown to be effective for treating, for example, neuropathic pain (see e.g., Non-patent Literatures 1 and 2).

Several types of $\alpha_2\delta$ ligands are currently known as therapeutic drugs for neuropathic pain. Examples of $\alpha_2\delta$ ligands include gabapentine and pregabalin. $\alpha_2\delta$ ligands such as these compounds are useful for treating epilepsy and neuropathic pain or the like (e.g., Patent Literature 1). Other compounds are disclosed in, for example, Patent Literatures 2, 3, and 4.

Also, the present applicant has previously reported an $\alpha_2\delta$ ligand and a method for producing the same in Patent Literatures 5 and 6.

CITATION LIST

Patent Literature

Patent Literature 1: US 2006/154929
Patent Literature 2: US 2003/220397
Patent Literature 3: US 2004/152779
Patent Literature 4: US 2003/78300
Patent Literature 5: US 2010/249229
Patent Literature 6: US 2010/110361

Non-Patent Literature

Non-patent Literature 1: J. Biol. Chem. 271 (10): 5768-5776, 1996
Non-patent Literature 2: J. Med. Chem. 41: 1838-1845, 1998

SUMMARY OF INVENTION

Technical Problem

An object of the present invention is to provide a method for producing a bicyclic γ-amino acid derivative or a pharmacologically acceptable salt thereof, particularly, a compound having activity as an $\alpha_2\delta$ ligand and an intermediate thereof.

While Patent Literature 5 or 6 has reported a production method as described in Scheme 1, the present inventors have continued diligent studies to tackle problems of (1) improving the yields of Step 1 to Step 4, (2) achieving production using more inexpensive starting materials, and (3) facilitating stirring in Step 4 to improve reproducibility. Consequently, the present inventors have solved the problems and completed the present invention.

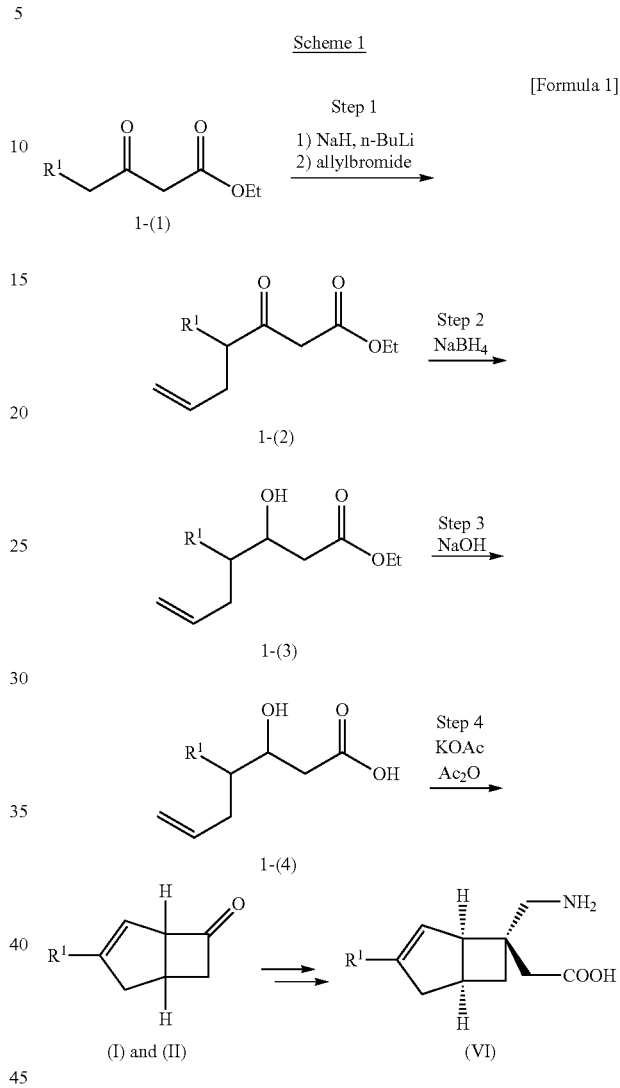

Scheme 1

[Formula 1]

wherein the substituent is defined as follows: $R^1$: a hydrogen atom or a C1-C6 alkyl group.

Solution to Problem

The present invention will be described below. [1] A method for producing a compound represented by the general formula (I) and a compound represented by the general formula (II):

[Formula 2]

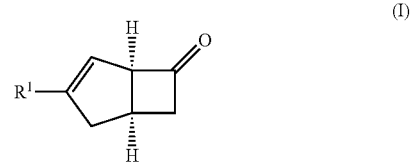

(I)

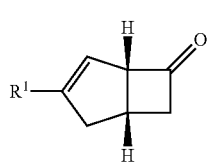

(II)

wherein the substituent is defined as follows: $R^1$: a hydrogen atom or a C1-C6 alkyl group, the method comprising (1) reacting a compound represented by the general formula (III) with an allyl halide to produce a compound represented by the general formula (IV):

[Formula 3]

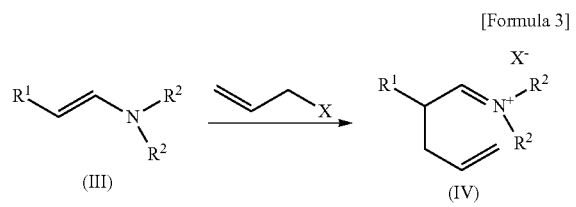

wherein each substituent is defined as follows:
$R^1$: a hydrogen atom or a C1-C6 alkyl group, $R^2$: a C1-C6 alkyl group, and X: a halogen atom, (2) reacting the compound represented by the general formula (IV) with malonic acid in the presence of a base or a base and a catalyst to produce a compound represented by the general formula (V):

[Formula 4]

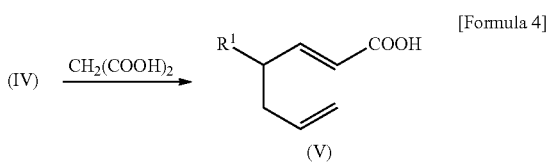

wherein the substituent is defined as follows: $R^1$: a hydrogen atom or a C1-C6 alkyl group, and (3) heating the compound represented by the general formula (V) in the presence of an acid anhydride and a tertiary amine to produce the compound represented by the general formula (I) and the compound represented by the general formula (II).

[2] The method according to [1], wherein $R^1$ is a methyl group or an ethyl group.

[3] The method according to [1] or [2], wherein $R^2$ is an isobutyl group.

[4] The method according to any one of [1] to [3], wherein the allyl halide used in (1) is allyl bromide.

[5] The method according to any one of [1] to [4], wherein the base used in (2) is pyridine.

[6] The method according to any one of [1] to [5], wherein the catalyst used in (2) is piperidine or morpholine.

[7] The method according to any one of [1] to [6], wherein the acid anhydride and the tertiary amine used in (3) are acetic anhydride and triethylamine, respectively.

[8] A method for producing a compound represented by the general formula (VI) or a salt thereof:

[Formula 5]

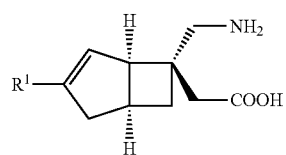

(VI)

wherein each substituent is defined as follows: $R^1$: a hydrogen atom or a C1-C6 alkyl group, the method comprising producing a compound represented by the general formula (I) and a compound represented by the general formula (II) by a method according to [1], and then producing the compound represented by the general formula (VI) or the salt thereof using the compound represented by the general formula (I) and the compound represented by the general formula (II).

[9] A compound represented by the general formula (IV):

[Formula 6]

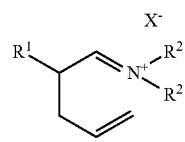

(IV)

wherein each substituent is defined as follows: $R^1$: a hydrogen atom or a C1-C6 alkyl group, $R^2$: a C1-C6 alkyl group, and X: a halogen atom.

Advantageous Effects of Invention

The production method according to the present invention can provide a bicyclic γ-amino acid derivative having excellent activity as an $α_2δ$ ligand, an intermediate for producing the same, or salts thereof.

The production method of the present invention can produce the compound of interest using only inexpensive starting materials and eliminates the need to use reagents having a high risk of igniting, such as sodium hydride, n-butyllithium, or sodium borohydride. Also, the production method of the present invention can efficiently produce the compound of interest because the method permits continuous production steps without isolating an iminium salt (IV).

DESCRIPTION OF EMBODIMENTS

A "C1-C6 alkyl group" refers to a linear or branched alkyl group having 1 to 6 carbon atoms and includes methyl, ethyl, propyl, isopropyl, butyl, isobutyl, sec-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl groups.

A "halogen atom" refers to a fluorine, chlorine, bromine, or iodine atom.

(1) Allylation Reaction (Scheme 2)

A compound represented by the general formula (III) is reacted with an allyl halide to produce a compound represented by the general formula (IV).

Scheme 2

[Formula 7]

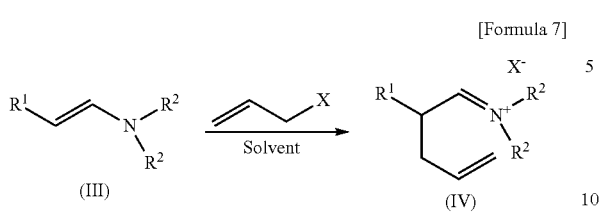

wherein each substituent is defined as follows: $R^1$: a hydrogen atom or a C1-C6 alkyl group, $R^2$: a C1-C6 alkyl group, and X: a halogen atom.

The allyl halide used in this reaction is allyl chloride, allyl bromide, or allyl iodide, preferably allyl bromide.

$R^1$ used in this reaction is preferably a methyl group or an ethyl group.

$R^2$ used in this reaction is preferably an n-propyl group, an n-butyl group, or an isobutyl group, particularly preferably an isobutyl group.

This reaction may be performed at room temperature and can be performed in a shorter time by heating to 60° C. or higher.

The solvent used in this reaction is preferably acetonitrile.

(2) Knoevenagel Condensation Reaction (Doebner Reaction, Scheme 3)

The compound represented by the general formula (IV) is reacted under conditions of Knoevenagel condensation reaction to produce a compound represented by the general formula (V).

Scheme 3

[Formula 8]

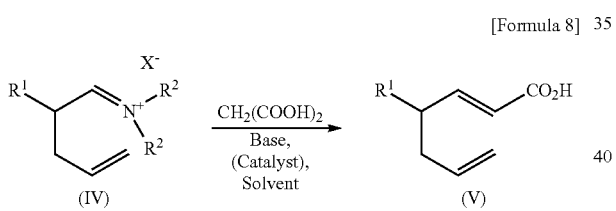

wherein each substituent is defined as follows: $R^1$: a hydrogen atom or a C1-C6 alkyl group, $R^2$: a C1-C6 alkyl group, and X: a halogen atom.

The base used in this reaction is preferably pyridine. The addition of, for example, piperidine or morpholine as a catalyst can smoothly promote the reaction.

This reaction proceeds by heating, preferably by heating at 70° C. or higher.

The solvent used in this reaction is preferably pyridine, acetonitrile, or toluene.

(3) [2+2] Cycloaddition Reaction

The compound represented by the general formula (V) is reacted under conditions of [2+2] cycloaddition reaction to produce a compound represented by the general formula (I) and a compound represented by the general formula (II).

[Formula 9]

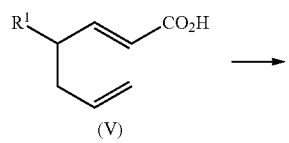

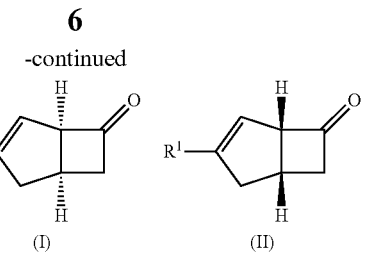

wherein each substituent is defined as follows: $R^1$: a hydrogen atom or a C1-C6 alkyl group.

The acid anhydride used in this reaction is preferably acetic anhydride, propionic anhydride, or butyric anhydride, more preferably acetic anhydride.

The tertiary amine used in this reaction is preferably triethylamine, tripropylamine, tributylamine, or N-methylmorpholine, more preferably triethylamine.

The solvent used in this reaction is preferably an aprotic solvent, more preferably N,N-dimethylformamide, N,N-dimethylacetamide, dimethyl sulfoxide, N-methyl-2-pyrrolidone, or 1,3-dimethyl-2-imidazolidinone, more preferably N,N-dimethylacetamide.

This reaction proceeds by heating. The reaction temperature is preferably 100 to 120° C. In this case, the reaction time is 5 to 10 hours.

A compound represented by the general formula (VI) can be produced by the method described in Patent Literature 6 (WO 2010/110361) above using the compound represented by the general formula (I) and the compound represented by the general formula (II).

[Formula 10]

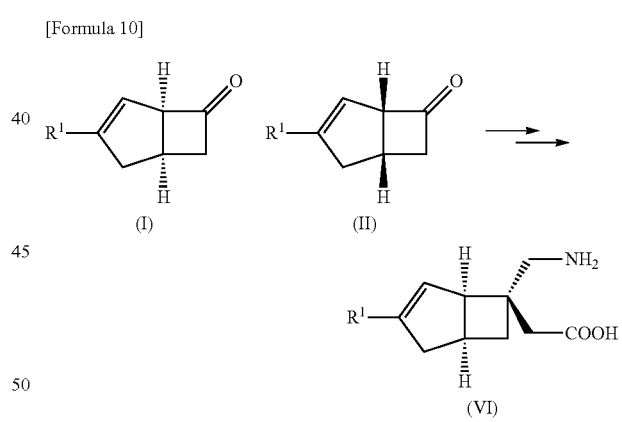

Since compounds represented by the general formula (VI), or the like, having amino and/or carboxyl groups in the structure, form salts through reaction with an acid or a base, a "salt" as used herein refers to these salts.

The compound represented by the general formula (VI), or the like, when left in the air or recrystallized, may associate with adsorbed water through water absorption to form a hydrate. Such hydrates are also encompassed by the salts of the present invention.

The compound represented by the general formula (VI) or a pharmacologically acceptable salt thereof exhibits activity as an $\alpha_2\delta$ ligand and affinity for voltage-dependent calcium channel subunit $\alpha_2\delta$ and is useful as an active ingredient in a pharmaceutical composition used for treating and/or preventing pain, central nervous system involvement, and other disorders.

EXAMPLES

Example 1

3-Ethylbicyclo[3.2.0]hept-3-en-6-one (1-a-1) (E)-but-1-enyldiisobutylamine (Dehydration and Reflux Method)

[Formula 11]

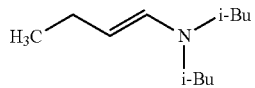

Butanal (68 mL, 0.75 mol) was added dropwise over 20 minutes to a solution of diisobutylamine (87 mL, 0.50 mol) in toluene (100 mL) at room temperature under a nitrogen atmosphere. After installation of a Dean-Stark tube, the mixture was warmed to 130° C. and refluxed. 50 mL of distillate containing water was extracted twice. The reaction mixture was cooled to room temperature and then distilled under reduced pressure (0.25 mmHg, 51-55° C.) to obtain the title compound (67.67 g, yield: 74%) as a colorless oil substance.

(1-a-2) (E)-But-1-enyldiisobutylamine (Dehydrating Agent Addition Method)

[Formula 12]

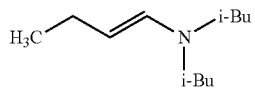

Potassium carbonate (4.8 g, 35 mmol) was added to diisobutylamine (17.5 mL, 0.10 mol) under a nitrogen atmosphere, and the mixture was then cooled to −7° C. Butanal (9.0 mL, 0.10 mol) was added dropwise thereto over 10 minutes. The reaction mixture was gradually heated to room temperature and stirred for 19 hours. Insoluble matter was filtered off, and the filtrate was then concentrated under reduced pressure to obtain the title compound (13.6 g, yield: 74%) as a colorless oil substance.

$^1$H NMR (400 MHz, CDCl$_3$) δ 0.82-0.94 (m, 15H), 1.83-1.97 (m, 4H), 2.70 (d, 4H, J=7.0 Hz), 4.02 (dt, 1H, J=7.0, 14.0 Hz), 5.92 (dd, 1H, J=1.0, 14.0 Hz).

(1-b) N,N-Diisobutyl-2-ethylpent-4-en-1-iminium bromide

[Formula 13]

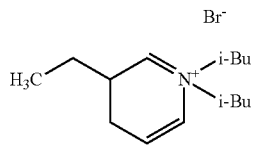

Allyl bromide (1.30 mL, 15 mmol) was added to a mixture of (E)-but-1-enyldiisobutylamine (1.83 g, 10 mmol) and acetonitrile (5.5 mL) at room temperature under a nitrogen atmosphere, and the mixture was then stirred at an external temperature of 60° C. for 15 hours. The reaction mixture was cooled to room temperature and then concentrated under reduced pressure to obtain the title compound (2.79 g, 92%) as a red purple solid.

$^1$H NMR (400 MHz, CDCl$_3$) δ 0.91-0.98 (m, 15H), 1.60-1.76 (m, 2H), 2.10-2.19 (m, 2H), 2.50-2.35 (m, 2H), 3.00-3.09 (m, 1H), 3.60-3.82 (m, 4H), 5.07-5.11 (m, 1H), 5.16-5.22 (m, 1H), 5.73-5.84 (m, 1H), 8.65 (d, 1H, J=10.5 Hz).

(1-c-1) (2E)-4-Ethylhepta-2,6-dienoic acid

[Formula 14]

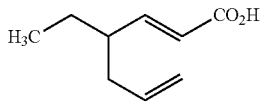

Allyl bromide (7.1 mL, 81.8 mmol) was added to a mixture of (E)-but-1-enyldiisobutylamine (10.0 g, 54.5 mmol) and acetonitrile (30 mL) at room temperature under a nitrogen atmosphere, and the mixture was then stirred at an external temperature of 70° C. for 17 hours. The reaction mixture was cooled to room temperature and then concentrated under reduced pressure to obtain an iminium salt as a red purple solid. The obtained iminium salt was dissolved in pyridine (100 mL). To the solution, malonic acid (11.3 g, 109.0 mmol) and piperidine (0.81 mL, 8.2 mmol) were then added in this order. The reaction mixture was stirred at an external temperature of 100° C. for 17 hours and then cooled to room temperature. Pyridine was distilled off, and the residue was then separated into aqueous and organic layers by the addition of ethyl acetate and 1 M hydrochloric acid. The organic layer was washed with saturated saline and then dried over anhydrous sodium sulfate. The solvent was distilled off, and the residue was then purified by silica gel chromatography (n-hexane:ethyl acetate=5:1→1:1) to obtain the title compound (6.96 g, yield: 83%) as a colorless oil substance.

$^1$H NMR (400 MHz, CDCl$_3$) δ 0.88 (t, 3H, J=7.4 Hz), 1.32-1.42 (m, 1H), 1.50-1.60 (m, 1H), 2.12-2.25 (m, 3H), 5.00-5.06 (m, 2H), 5.65-5.76 (m, 1H), 5.80 (d, 1H, J=15.8 Hz), 6.90 (dd, 1H, J=8.4, 15.8 Hz).

(1-c-2) (2E)-4-Ethylhepta-2,6-dienoic acid (One-Pot Method)

[Formula 15]

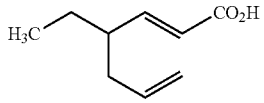

Allyl bromide (75 mL, 0.865 mol) was added dropwise over 10 minutes to a mixture of (E)-but-1-enyldiisobutylamine (122 g, 0.665 mol) and acetonitrile (370 mL) at room temperature under a nitrogen atmosphere, and the mixture was then stirred for 20 minutes. The reaction mixture was heated and stirred at an external temperature of 70° C. for 17 hours, followed by attachment of a Dean-Stark tube. The external temperature was set to 115° C., and approximately 120 mL of distillate was extracted. Then, acetonitrile (360 mL) was added thereto. Approximately 120 mL of distillate was extracted again and then cooled to room temperature. To the obtained reaction mixture, pyridine (108 mL, 1.33 mol), piperidine (10 mL, 0.1 mol), and malonic acid (104 g, 0.998 mol) were added in this order, and the mixture was then stirred at an external temperature of 100° C. for 17 hours. After cooling to room temperature, approximately 430 mL of the solvent was distilled off under reduced pressure. The pH of the reaction mixture was adjusted to 1 by the addition of 6 M hydrochloric acid (200 mL), followed by extractions with toluene (250 mL×2 and 120 mL×1). After extractions into aqueous layers with a 3 M aqueous sodium hydroxide solution (200 mL×2 and 100 mL×1), the pH of the extracts was adjusted to 1 with concentrated hydrochloric acid (100 mL). After extractions with toluene (200 ml×2), the organic layer was concentrated under reduced pressure. To the residue, toluene (200 mL) was added, and insoluble matter was then filtered off. The filtrate was concentrated under reduced pressure to obtain 98.1 g of a crude product of the title compound as a colorless oil substance. As a result of quantitative analysis by HPLC, the yield was 86% through two steps from (E)-but-1-enyldiisobutylamine.

(1-d) 3-Ethylbicyclo[3.2.0]hept-3-en-6-one

[Formula 16]

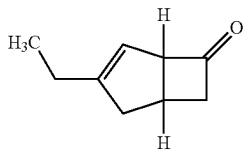

(2E)-4-Ethylhepta-2,6-dienoic acid (34.0 g, purity: 90.7%) was dissolved in N,N-dimethylacetamide (100 mL) under the nitrogen atmosphere. To the solution, acetic anhydride (37.8 mL, 0.40 mol) and triethylamine (28 mL, 0.20 mol) were added. The reaction mixture was warmed and stirred at 105 to 115° C. for 6.5 hours. The reaction mixture was cooled to room temperature, and water (200 mL) was added thereto, followed by four extractions with n-hexane (150 mL×2 and 50 mL×2). All the extracted organic layers were combined and then washed with a saturated aqueous solution of sodium bicarbonate (50 mL) and water (50 mL) in this order. The obtained organic layer was concentrated under reduced pressure, and the residue was distilled under reduced pressure (93-102° C., approximately 25 mmHg) to obtain the title compound (22.06 g, colorless oil substance) (yield: 81%).

$^1$H NMR (400 MHz, CDCl$_3$) δ 1.07 (t, 3H, J=7.4 Hz), 2.14 (q, 2H, J=7.4 Hz), 2.28-2.34 (m, 1H), 2.75-2.86 (m, 3H), 3.16-3.25 (m, 1H), 4.16-4.22 (m, 1H), 5.20-5.24 (m, 1H).

Reference Example 1

[6-Aminomethyl-3-ethylbicyclo[3.2.0]hept-3-en-6-yl]acetic acid

[Formula 17]

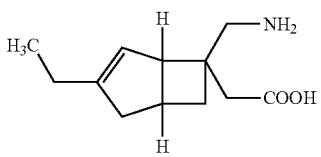

(1-a) Ethyl 4-ethyl-3-hydroxyhept-6-enoate

Sodium hydride (>63% oil, 2.09 g, 55 mmol) was added to a solution of ethyl 3-oxohexanoate (7.91 g, 50 mmol) in tetrahydrofuran (50 mL) under ice cooling, and the mixture was stirred in this state for 10 minutes. To the reaction solution, n-butyllithium (1.58 M solution in hexane, 34.8 mL, 55 mmol) was added dropwise, and the mixture was further stirred for 10 minutes under ice cooling. Then, allyl bromide (4.7 mL, 55 mmol) was added thereto, and the mixture was stirred in this state for 1 hour and then further stirred at room temperature for 4 hours. To the reaction solution, 1 N hydrochloric acid and a saturated aqueous solution of ammonium chloride were added, followed by extraction with n-pentane. The organic layer was washed with saturated saline and dried over anhydrous magnesium sulfate, and the solvent was distilled off under reduced pressure. The obtained residue was dissolved in ethanol (80 mL). To the solution, sodium borohydride (1.51 g, 40 mmol) was added under ice cooling, and the mixture was stirred in this state for 2 hours. 1 N hydrochloric acid (50 mL) was added thereto, and the mixture was stirred for 30 minutes. Then, saturated saline was added thereto, followed by extraction with ethyl acetate. The organic layer was washed with saturated saline and then dried over anhydrous magnesium sulfate, and the solvent was distilled off under reduced pressure. The residue was purified by silica gel column chromatography to obtain the compound of interest as a pale yellow oil substance (3.64 g, 37%, mixture of diastereomers).

$^1$H-NMR (400 MHz, CDCl$_3$): δ ppm: 0.91 (3H, t, J=7.5 Hz), 1.28 (3H, t, J=7.2 Hz), 1.43-1.55 (2H, m), 1.98-2.28 (2H, m), 2.45-2.48 (2H, m), 2.88-2.93 (1H, m), 4.07-4.10 (1H, m), 4.10-4.20 (2H, m), 5.01-5.09 (2H, m), 5.75-5.86 (1H, m).

(1-b) 4-Ethyl-3-hydroxyhept-6-enoic acid

Ethyl 4-ethyl-3-hydroxyhept-6-enoate (3.64 g, 18.2 mmol) was dissolved in a 2 N solution of potassium hydroxide in methanol (120 mL), and the solution was stirred overnight at room temperature. From the reaction solution, the solvent was distilled off under reduced pressure. To the residue, a 1 N aqueous sodium hydroxide solution (200 mL) was then added, followed by extraction with diethyl ether. The aqueous layer was made acidic by the addition of concentrated hydrochloric acid under ice cooling, followed by extraction with diethyl ether again. The organic layer was washed with saturated saline and dried over anhydrous magnesium sulfate. Then, the solvent was distilled off under reduced pressure to obtain the compound of interest as a pale yellow oil substance (3.14 g, <100%, mixture of diastereomers).

$^1$H-NMR (400 MHz, CDCl$_3$): δ ppm: 0.91-0.96 (3H, m), 1.39-1.52 (3H, m), 2.01-2.28 (2H, m), 2.52-2.55 (2H, m), 4.05-4.15 (2H, m), 5.03-5.10 (2H, m), 5.74-5.86 (1H, m).

(1-c) Tert-butyl 3-ethylbicyclo[3.2.0]hept-3-en-6-ylideneacetate

4-Ethyl-3-hydroxyhept-6-enoic acid (3.13 g, 18.2 mmol) was dissolved in acetic anhydride (15 mL). To the solution, potassium acetate (4.27 g, 43.6 mmol) was added, and the mixture was stirred at room temperature for 100 minutes. The reaction solution was heated to reflux and stirred for 3.5 hours to form "3-ethylbicyclo[3.2.0]hept-6-en-6-one" in the reaction solution. To the reaction solution, ice water and toluene were then added, and this mixture was stirred overnight at room temperature. The mixture was separated into aqueous and organic layers by the addition of saturated saline (50 mL)

and toluene (20 mL). Then, the organic layer was washed with a 1 N aqueous sodium hydroxide solution and saturated saline in this order, then dried over anhydrous magnesium sulfate, and filtered. The filtrate was added to a reaction solution prepared by adding sodium hydride (>65% oil, 761.9 mg, 20 mmol) to a solution of tert-butyl dimethoxyphosphorylacetate (4.48 g, 20 mmol) in tetrahydrofuran (50 mL) under ice cooling, and the mixture was further stirred for 1 hour. The reaction solution was separated into aqueous and organic layers by the addition of a saturated aqueous solution of ammonium chloride and saturated saline. The aqueous layer was subjected to extraction with ethyl acetate. The organic layers were combined, then washed with saturated saline, and then dried over anhydrous magnesium sulfate. The solvent was distilled off under reduced pressure, and the residue was purified by silica gel column chromatography to obtain the compound of interest as a pale yellow oil substance (1.32 g, 31%, E/Z mixture).

$^1$H-NMR (400 MHz, CDCl$_3$): δ ppm:

Major isomer: 1.06 (3H, t, J=7.4 Hz), 1.45 (9H, s), 2.07-2.22 (3H, m), 2.59-2.70 (2H, m), 2.87-2.96 (1H, m), 3.30 (1H, ddt, J=8.6, 18.4, 2.7 Hz), 3.86-3.88 (1H, m), 5.22-5.23 (1H, m), 5.45-5.47 (1H, m).

Minor isomer: 1.08 (3H, t, J=7.3 Hz), 1.49 (9H, s), 2.07-2.21 (3H, m), 2.43-2.47 (1H, m), 2.59-2.70 (1H, m), 2.75-2.85 (1H, m), 2.87-2.96 (1H, m), 4.28-4.31 (1H, m), 5.35-5.38 (1H, m), 5.45-5.47 (1H, m).

(1-d) Tert-butyl [3-ethyl-6-(nitromethyl)bicyclo[3.2.0]hept-3-en-6-yl]acetate

Tert-butyl 3-ethylbicyclo[3.2.0]hept-3-en-6-ylideneacetate (1.32 g, 5.63 mmol) was dissolved in nitromethane (7 mL). To the solution, 1,8-diazabicyclo[5.4.0]undec-7-ene (1.2 mL, 7.3 mmol) was added, and the mixture was heated with stirring at 50 to 60° C. for 7 hours. The mixture was allowed to cool, and a saturated aqueous solution of potassium dihydrogen phosphate was then added thereto, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (1.39 g, 84%).

$^1$H-NMR (400 MHz, CDCl$_3$): δ ppm: 1.09 (3H, t, J=7.4 Hz), 1.46 (9H, s), 1.52 (1H, dd, J=7.6, 13.2 Hz), 2.06 (1H, d, 16.6 Hz), 2.14 (2H, q, J=7.4 Hz), 2.30 (1H, ddd, J=2.4, 7.6, 13.2 Hz), 2.47 (2H, s), 2.49 (1H, dd, J=7.6, 16.6 Hz), 2.86 (1H, quint, J=7.6 Hz), 3.21-3.22 (1H, m), 4.75 (1H, d, J=11.7 Hz), 4.84 (1H, d, J=11.7 Hz), 5.27 (1H, s).

(1-e) [6-Aminomethyl-3-ethylbicyclo[3.2.0]hept-3-en-6-yl]acetic acid

Tert-butyl [3-ethyl-6-(nitromethyl)bicyclo[3.2.0]hept-3-en-6-yl]acetate (1.09 g, 4.71 mmol) was dissolved in ethanol (10 mL) and water (5 mL). To the solution, iron powder (1.32 g, 23.5 mmol) and ammonium chloride (249.6 mg, 4.71 mmol) were added, and the mixture was stirred for 2 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate, and the solvent was then distilled off under reduced pressure. To the residue, a 4 N solution of hydrochloric acid in ethyl acetate (20 mL) was added, and the mixture was stirred at room temperature for 1 hour. Then, the solvent was distilled off under reduced pressure. The residue was suspended in dichloromethane. To the suspension, triethylamine was added dropwise, and the resulting powder was collected by filtration, then washed with dichloromethane, and then dried to obtain the compound of interest as a white powder (425.1 mg, 43%).

$^1$H-NMR (400 MHz, CD$_3$OD): δ ppm: 1.10 (3H, t, J=7.4 Hz), 1.48 (1H, dd, J=7.5, 12.5 Hz), 2.03-2.08 (2H, m), 2.14 (2H, q, J=7.4 Hz), 2.46 (1H, d, J=16.2 Hz), 2.46-2.53 (1H, m), 2.51 (1H, d, J=16.2 Hz), 2.85 (1H, quint, J=7.5 Hz), 3.09-3.10 (1H, m), 3.14 (1H, d, J=13.0 Hz), 3.18 (1H, d, J=13.0 Hz), 5.38 (1H, dd, J=1.7, 3.7 Hz).

(Step of Performing Optical Resolution from Diastereomeric Mixture)

Reference Example 2

Tert-butyl [(1R,5S,6S)-6-aminomethyl-3-ethylbicyclo[3.2.0]hept-3-en-6-yl]acetate D-mandelate

[Formula 18]

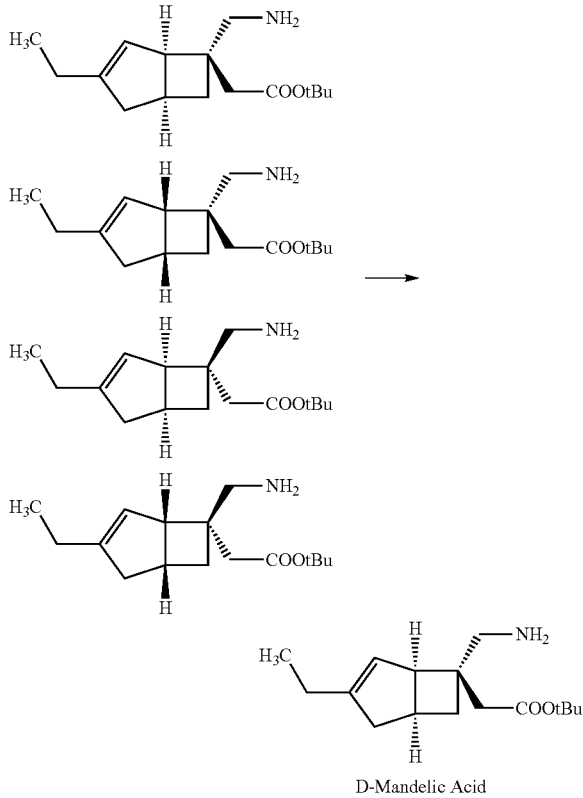

Acetonitrile (4.7 L, 8.6 v/w) was added to tert-butyl [6-aminomethyl-3-ethylbicyclo[3.2.0]hept-3-en-6-yl]acetate (627.0 g, net: 543.6 g, 2.05 mol, 85:15 diastereomeric mixture), and the mixture was stirred at 40° C. To the reaction solution, D-mandelic acid (116.3 g, 0.76 mmol, 0.37 eq.) was added, and the mixture was stirred at 40° C. for 1 hour and then allowed to cool slowly to 3° C. After stirring at 3° C. for 1 hour, the resulting crystal was collected by filtration. Then, the crystal was dried under reduced pressure under the condition of 40° C. to obtain tert-butyl [(1R,5S,6S)-6-aminomethyl-3-ethylbicyclo[3.2.0]hept-3-en-6-yl]acetate D-mandelate as a white powder (251.2 g, yield: 29.4%, 97.6% ee, 99.6% de).

$^1$H-NMR (400 MHz, DMSO-d6) δ ppm: 1.04 (3H, t, J=7.6 Hz), 1.28-1.35 (1H, m), 1.39 (9H, s), 1.96-2.11 (4H, m), 2.28 (1H, d, J=15.6 Hz), 2.33 (1H, d, J=15.6 Hz), 2.36-2.40 (1H, m), 2.72 (1H, quint, J=7.6 Hz), 3.00 (1H, d, J=13.2 Hz), 3.03 (1H, d, J=13.2 Hz), 3.31 (1H, br s), 4.54 (1H, s), 5.21-5.23 (1H, m), 7.13-7.25 (3H, m), 7.35-7.37 (2H, m).

$[α]_{20}^D$ −104.4° (C=0.108, MeOH).

Anal. calcd for $C_{24}H_{35}NO_5$: C, 69.04; H, 8.45; N, 3.35. Found C, 69.15; H, 8.46; N, 3.46.

The invention claimed is:

1. A method for producing a compound of general formula (I) and a compound of general formula (II):

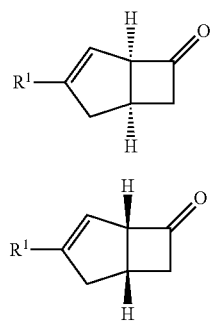

comprising:

(1) reacting a compound of general formula (III) with an allyl halide to produce a compound of general formula (IV):

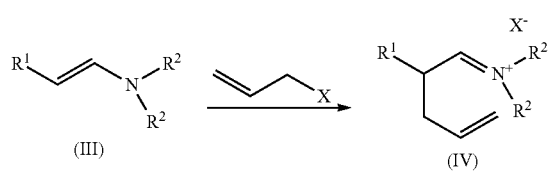

(2) reacting the compound of general formula (IV) with malonic acid in the presence of a base or a base and a catalyst to produce a compound of general formula (V):

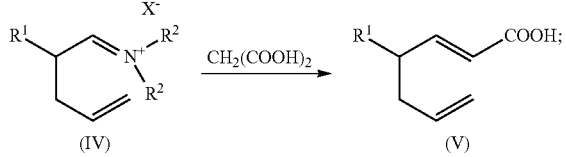

and (3) heating the compound of general formula (V) in the presence of an acid anhydride and a tertiary amine to produce the compound of general formula (I) and the compound of general formula (II);

wherein $R^1$ is a hydrogen atom or a C1-C6 alkyl group, $R^2$ is a C1-C6 alkyl group, and X is a halogen atom.

2. The method of claim 1, wherein $R^1$ is a methyl group or an ethyl group.

3. The method of claim 1, wherein $R^2$ is an isobutyl group.

4. The method of claim 1, wherein the allyl halide is allyl bromide.

5. The method of claim 1, wherein the base is pyridine.

6. The method of claim 1, wherein, in step (2), the reacting is in the presence of a base and a catalyst, and the catalyst is piperidine or morpholine.

7. The method of claim 1, wherein the acid anhydride is acetic anhydride and the tertiary amine is triethylamine.

8. A compound of general formula (IV):

wherein $R^1$ is a hydrogen atom or a C1-C6 alkyl group, $R^2$ is a C1-C6 alkyl group, and X is a halogen atom.

* * * * *